US010119982B2

(12) United States Patent
Baer (10) Patent No.: US 10,119,982 B2
(45) Date of Patent: Nov. 6, 2018

(54) TRANSPORT CARRIER, LABORATORY CARGO DISTRIBUTION SYSTEM, AND LABORATORY AUTOMATION SYSTEM

(71) Applicant: Roche Diagnostics Operations, Inc., Indianapolis, IN (US)

(72) Inventor: Jonathan Baer, Stuttgart (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/056,265

(22) Filed: Feb. 29, 2016

(65) Prior Publication Data

US 2016/0274137 A1   Sep. 22, 2016

(30) Foreign Application Priority Data

Mar. 16, 2015   (EP) .................................. 15159299

(51) Int. Cl.
| | |
|---|---|
| *B01L 9/06* | (2006.01) |
| *G01N 35/04* | (2006.01) |
| *B65G 43/00* | (2006.01) |
| *B65G 54/02* | (2006.01) |
| *G01N 35/00* | (2006.01) |

(52) U.S. Cl.
CPC .............. *G01N 35/04* (2013.01); *B65G 43/00* (2013.01); *B65G 54/02* (2013.01); *G01N 35/00871* (2013.01); *G01N 2035/046* (2013.01); *G01N 2035/0477* (2013.01)

(58) Field of Classification Search
USPC .......... 422/560–562; 193/35 R, 44; 198/300, 198/347.1, 348, 350, 373, 418, 690.1; 406/1; 901/1
See application file for complete search history.

(56) References Cited

U.S. PATENT DOCUMENTS

| | | | |
|---|---|---|---|
| 3,273,727 | A | 9/1966 | Rogers et al. |
| 3,653,485 | A | 4/1972 | Donlon |
| 3,901,656 | A | 8/1975 | Durkos et al. |
| 4,150,666 | A | 4/1979 | Brush |
| 4,395,164 | A | 7/1983 | Beltrop |
| 4,544,068 | A | 10/1985 | Cohen |
| 4,771,237 | A | 9/1988 | Daley |
| 5,120,506 | A | 6/1992 | Saito et al. |
| 5,295,570 | A | 3/1994 | Grechsch et al. |
| 5,309,049 | A | 5/1994 | Kawada et al. |
| 5,523,131 | A | 6/1996 | Isaacs et al. |
| 5,530,345 | A | 6/1996 | Murari et al. |
| 5,636,548 | A | 6/1997 | Dunn et al. |

(Continued)

FOREIGN PATENT DOCUMENTS

| | | |
|---|---|---|
| CN | 201045617 Y | 4/2008 |
| CN | 201190033 Y | 2/2009 |

(Continued)

*Primary Examiner* — Dean Kwak
(74) *Attorney, Agent, or Firm* — Roche Diagnostics Operations, Inc.

(57) ABSTRACT

A transport carrier for a laboratory cargo distribution system with a transport plane is disclosed. The transport carrier can be rotationally moved in an easily controllable manner on the transport plane. A laboratory cargo distribution system with a transport plane comprising such a transport carrier and a laboratory automation system comprising such a laboratory cargo distribution system are also disclosed.

11 Claims, 3 Drawing Sheets

(56) References Cited

U.S. PATENT DOCUMENTS

| | | |
|---|---|---|
| 5,641,054 A | 6/1997 | Mori et al. |
| 5,651,941 A | 7/1997 | Stark et al. |
| 5,720,377 A * | 2/1998 | Lapeus ............... B01L 9/06 198/346.1 |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Talmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokol et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 * | 9/2014 | Stoeckle ............ B65G 19/24 198/619 |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,352,899 B2 | 5/2016 | Mueller et al. |
| 9,423,410 B2 | 8/2016 | Buehr |
| 9,423,411 B2 | 8/2016 | Riether |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2014/0234978 A1 | 8/2014 | Heise et al. |
| 2015/0014125 A1 | 1/2015 | Hecht |
| 2015/0166265 A1 | 6/2015 | Pollack et al. |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |

(56) References Cited

U.S. PATENT DOCUMENTS

| | | | |
|---|---|---|---|
| 2018/0074087 A1 | 3/2018 | Heise et al. | |
| 2018/0106821 A1 | 4/2018 | Vollenweider et al. | |
| 2018/0156835 A1 | 6/2018 | Hassan | |

FOREIGN PATENT DOCUMENTS

| | | |
|---|---|---|
| CN | 102109530 A | 6/2011 |
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | H01-266860 A | 10/1989 |
| JP | H02-87903 A | 3/1990 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-026808 A | 4/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H08-265914 A | 10/1996 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 A | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 1996036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013152089 A1 | 10/2013 |
| WO | 2013/169778 A1 | 11/2013 |
| WO | 2013177163 A1 | 11/2013 |
| WO | 2014/059134 A1 | 4/2014 |
| WO | 2014071214 A1 | 5/2014 |

* cited by examiner

TRANSPORT CARRIER, LABORATORY CARGO DISTRIBUTION SYSTEM, AND LABORATORY AUTOMATION SYSTEM

CROSS-REFERENCE TO RELATED APPLICATIONS

This application claims priority to EP 15159299.5, filed Mar. 16, 2015, which is hereby incorporated by reference.

BACKGROUND

The present disclosure relates to a transport carrier for a laboratory cargo distribution system, to a laboratory cargo distribution system comprising such a transport carrier and to a laboratory automation system comprising such a laboratory cargo distribution system.

Known laboratory cargo distribution systems are typically used in laboratory automation systems in order to distribute laboratory cargo, i.e. samples contained in sample container carriers, between different laboratory stations by means of transport carriers.

Therefore, there is a need for a transport carrier having more functionalities than transport carriers of the prior art and to provide a laboratory cargo distribution system comprising such a transport carrier and to provide a laboratory automation system comprising such a laboratory cargo distribution system.

SUMMARY

According to the present disclosure, a transport carrier for a laboratory cargo distribution system, a laboratory distribution system and a laboratory automation system are provided. The laboratory cargo distribution system can comprises a transport plane and a plurality of electro-magnetic actuators stationary arranged relative to the transport plane. The transport carrier can comprise a first magnetically active device to interact with a first magnetic field generated by a first group of electro-magnetic actuators chosen from the plurality of electro-magnetic actuators such that a first magnetic move force is applied to the transport carrier, a second magnetically active device to interact with a second magnetic field generated by a second group of electro-magnetic actuators chosen from the plurality of electro-magnetic actuators such that a second magnetic move force is applied to the transport carrier, and a guidance. The guidance can be adapted to guide the first magnetically active device such that a distance between the first magnetically active device and the second magnetically active device is variable during a rotational movement of the transport carrier on the transport plane. The transport carrier can carry a laboratory cargo and can move over the transport plane.

Accordingly, it is a feature of the embodiments of the present disclosure to provide for a transport carrier having more functionalities than transport carriers of the prior art and to provide a laboratory cargo distribution system comprising such a transport carrier and to provide a laboratory automation system comprising such a laboratory cargo distribution system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A transport carrier for a laboratory cargo distribution system is presented. The laboratory cargo distribution system can comprise a transport plane and a plurality of electro-magnetic actuators stationary arranged relative to, in particular below, the transport plane. The transport carrier can be adapted to carry a laboratory cargo. Furthermore, the transport carrier can be adapted to be moved over the transport plane. The transport carrier can comprise a first magnetically active device adapted to interact with a first magnetic field generated by a first group of electro-magnetic actuators chosen from the plurality of electro-magnetic actuators such that a first magnetic move force can be applied to the transport carrier. Moreover, the transport carrier can comprise a second magnetically active device adapted to interact with a second magnetic field generated by a second group of electro-magnetic actuators chosen from the plurality of electro-magnetic actuators such that a second magnetic move force can be applied to the transport carrier. Additionally, the transport carrier can comprise a guidance. The guidance can be adapted to guide the first magnetically active device, such that a distance between the first magnetically active device and the second magnetically active device can be variable during a rotational movement of the transport carrier on the transport plane. In particular, the guidance may allow a translational movement of the first magnetically active device in the transport carrier. In particular, the distance between the first magnetically active device and the second magnetically active device may be variable parallel to the transport plane, when the transport carrier is placed on the transport plane.

The laboratory cargo may comprise or be a plurality of sample containers and/or a plurality of sample container carrier racks and/or laboratory equipment. The sample containers can be typically designed as tubes made of glass or transparent plastic and can typically have an opening at an upper end. The sample containers can be used to contain, store and transport samples such as blood samples or chemical samples. The sample container carrier racks can be used to store and contain sample containers. The laboratory equipment may comprise or be a plurality of laboratory instruments and/or a plurality of analysis liquid containers. The transport plane may also be denoted as transport surface. The transport plane can support the transport carrier, which may also be denoted as carrying the transport carrier. The electro-magnetic actuators can typically be solenoids surrounding ferromagnetic cores. The first group and the second group of electro-magnetic actuators can be energized or driven in order to generate the first magnetic field and the second magnetic field, respectively. The first group and the second group can include one or more electro-magnetic actuators, respectively, whereby an electro-magnetic actuator may be part of both groups. The first magnetic field and the second magnetic field may be part of a common magnetic field. The first magnetically active device can differ from the second magnetically active device. The first magnetically active device and the second magnetically active device may be a permanent magnet, respectively. Alternatively or additionally, an electro-magnet and/or any magnetically soft material may be used. The transport carrier can be translationally moved in two dimensions on the transport plane and can be rotationally moved around a normal to the transport plane by the first magnetic move force and/or the second magnetic move force. For that purpose, the electro-magnetic actuators may be arranged in two dimensions relative to the transport plane, in particular in a plane parallel to the transport plane.

The guidance can enable performing a rotational movement of the transport carrier on the transport plane in an improved manner compared to a transport carrier comprising a first magnetically active device and a second magnetically active device, which are both stationary fixed within the transport carrier. A choice of electro-magnetic actuators for the first group of electro-magnetic actuators and/or the second group of electro-magnetic actuators for the rotational movement and a control of the rotational movement by driving the first group and/or the second group can be simplified.

According to an embodiment, the guidance can comprise, in one embodiment can be, a linear guidance. Linear guidance can mean that the first magnetically active device can be translationally movable along a straight line within the transport carrier. This straight line may be parallel to a straight line between the first magnetically active device and the second magnetically active device. In one embodiment, the linear guidance may be oriented within the transport carrier in such a manner that it is parallel to the transport plane, when the transport carrier is placed on the transport plane.

According to an embodiment, the transport carrier can comprise a base body. The guidance can comprise a groove formed in the base body. The first magnetically active device can be, in particular, translationally movable, arranged in the groove.

According to an embodiment, the transport carrier can comprise a cargo platform. The cargo platform can be adapted to carry or support the laboratory cargo and a plurality of fixing devices adapted to fix the laboratory cargo relative to, in particular on, the cargo platform. The cargo platform may be on the base body, if existent. The fixing devices can prevent the carried laboratory cargo from sliding off the cargo platform as well as from tilting. In particular, this may allow avoiding spilling samples out of sample containers having an open upper end. The fixing devices may comprise pillars, ramps and/or walls.

According to an embodiment, the transport container can comprise a sliding surface. The sliding surface can be adapted to be in contact with the transport plane when the transport carrier is placed on the transport plane. The sliding surface can enable performing rotational movements of the transport carrier on the transport plane in an easy way. The sliding surface may be an underside of the base body, if existent.

The guidance may be adapted to guide the second magnetically active device as well. However, according to an embodiment, the second magnetically active device can be stationary fixed within the transport carrier. This can allow stationary fixing the part of the transport carrier, in which the second magnetically active device is stationary fixed, relative to the transport plane and thereby defining a rotational axis of the transport carrier, around which the transport carrier can be rotationally moved on the transport plane.

According to an embodiment, the guidance can have a first limiting stopper defining a minimum distance between the first magnetically active device and the second magnetically device and the guidance can have a second limiting stopper defining a maximum distance between the first magnetically active device and the second magnetically device. This can make it simpler to control movements of the transport carrier on the transport plane, in particular, when the transport carrier and/or the first magnetically active device within the transport carrier have been accidentally displaced.

The minimum distance and the maximum distance may be adapted or correspond to distances between the electro-magnetic actuators. Such a configuration may allow a better movement contribution of both magnetically active devices to translational movements of the transport carrier. According to an embodiment, the plurality of electro-magnetic actuators can be arranged in rows and columns. The electro-magnetic actuators can be equidistantly spaced within the rows and the columns by an adjacent distance. The minimum distance can correspond to the adjacent distance or a multiple of it. The maximum distance can corresponds to sqrt2 times the minimum distance. Thereby, the first magnetically active device can describe the form of a square on the transport plane during a 360° rotation of the transport carrier while being able to contribute, in particular together with the second magnetically active, to translational movements of the transport carrier. A multiple can be a natural number like 2, 3, 4 and the like.

According to an embodiment, the transport carrier can comprise a third magnetically active device adapted to interact with a third magnetic field generated by a third group of electro-magnetic actuators chosen from the plurality of electro-magnetic actuators such that a third magnetic move force can be applied to the transport carrier. The guidance can be adapted to guide the third magnetically active device, such that a distance between the first magnetically active device and the third magnetically active device and/or a distance between the second magnetically active device and the third magnetically active device can be variable during a rotational movement of the transport carrier on the transport plane. In particular, the third magnetically active device may be mirror symmetrically arranged within the transport carrier to the first magnetically active device with respect to a plane through a center of the second magnetically active device. The third group can include one or more electro-magnetic actuators, whereby an electro-magnetic actuator may be part of at least more than one group. The third magnetic field may be part of a common magnetic field with the first magnetic field and/or the second magnetic field. The third magnetically active device can differ from the first magnetically active device and the second magnetically active device. However, generally the above discussed for the first magnetically active device and the second magnetically active device may also be applicable for the third magnetically active device.

A laboratory cargo distribution system comprising a number of transport carriers as described above, a transport plane adapted to support or carry the transport carriers, a plurality of electro-magnetic actuators stationary arranged below the transport plane, in particular, in a plane parallel to the transport plane is presented. The electro-magnetic actuators can be adapted to generate magnetic fields to translationally and rotationally move the transport carriers on top of the transport plane. The laboratory cargo distribution system can also comprise a control device configured to control the translational and rotational movement of the transport carriers on top of the transport plane by driving first groups of electro-magnetic actuators chosen from the plurality of electro-magnetic actuators and/or by driving second groups of electro-magnetic actuators chosen from the plurality of electro-magnetic actuators such that the transport carriers move along corresponding, in particular, individual, transport paths. If the transport carriers comprise third magnetically active devices, the control device may be configured to control the movement of the transport carriers on top of the transport plane by driving third groups of electro-magnetic actuators chosen from the plurality of electro-magnetic actuators as well.

According to an embodiment, the plurality of electro-magnetic actuators can be arranged in rows and columns. The electro-magnetic actuators can be equidistantly spaced within the rows and the columns by an adjacent distance. In particular, in each second row in each second position there may be no electro-magnetic actuator. Thereby, the electro-magnetic actuators can form quadrats. In each center of a quadrant, no electro-magnetic actuator can be arranged.

A laboratory automation system comprising a number of laboratory stations, in the form of pre-analytical stations, analytical stations and/or post-analytical stations, and a laboratory cargo distribution system as described above adapted to distribute laboratory cargo between the laboratory stations is presented. The laboratory stations may be arranged adjacent to the laboratory cargo distribution system. Pre-analytical stations may be adapted to perform any kind of pre-processing of samples, sample containers, sample container carriers and/or sample container carrier racks. Analytical stations may be adapted to use a sample or part of the sample and a reagent to generate a measuring signal, the measuring signal indicating if and in which concentration, if any, an analyte exists. Post-analytical stations may be adapted to perform any kind of post-processing of samples, sample containers, sample container carriers and/or sample container carrier racks. The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station. Additionally, they may comprise at least one pushing station, belt station, conveying system station and/or gripper station for moving the laboratory cargo to or from the transport carrier.

By use of the transport carrier, the advantages of the transport carrier, as discussed above, can be made applicable for the laboratory cargo distribution system and the laboratory automation system, respectively.

Figure 1:
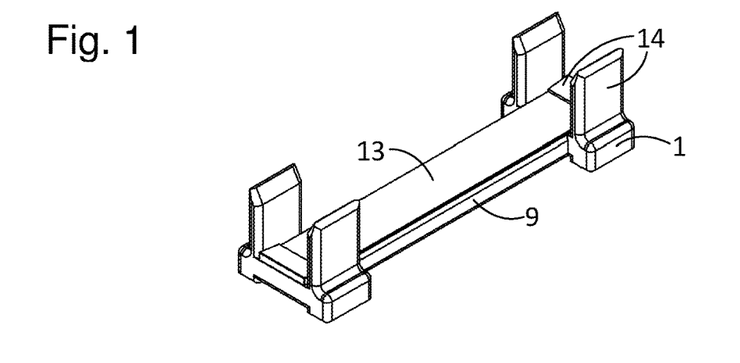
FIG. 1 illustrates a perspective view of a transport carrier according to an embodiment of the present disclosure.
Figure 2:
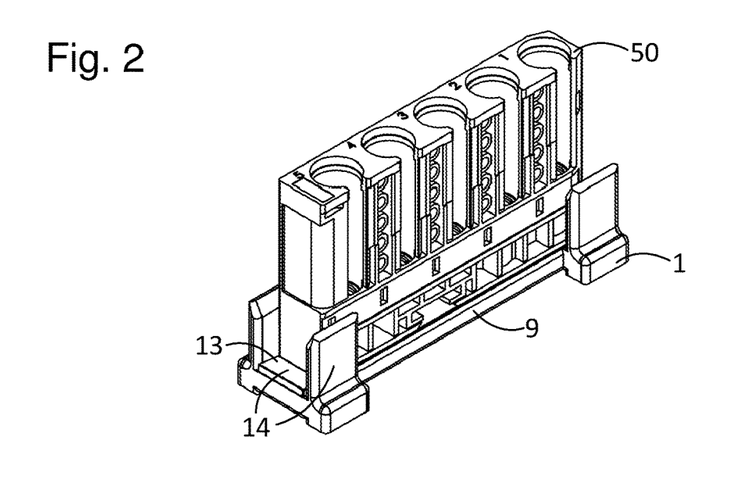
FIG. 2 illustrates a perspective view of the transport carrier of FIG. 1 carrying laboratory cargo according to an embodiment of the present disclosure.

FIGS. 1 and 2 show a transport carrier 1 of a laboratory cargo distribution system 100. The transport carrier 1 can be adapted to carry a laboratory cargo 50, which is in this embodiment a sample container carrier rack. The sample container carrier rack can be used to store and contain sample containers. The sample containers can be used to contain, store and transport samples. The transport carrier 1 can comprise a cargo platform 13 and a plurality of fixing devices 14. The cargo platform 13 can be adapted to carry or support the laboratory cargo 50. The transport carrier 1 can comprise a base body 9. The cargo platform 13 can be on the base body. The plurality of fixing devices 14 can be adapted to fix the laboratory cargo 50 relative to, in particular on, the cargo platform 13. The fixing devices 14 in the form of pillars and ramps can prevent the carried laboratory cargo 50 from sliding off the cargo platform 13 as well as from tilting.

Figure 3:
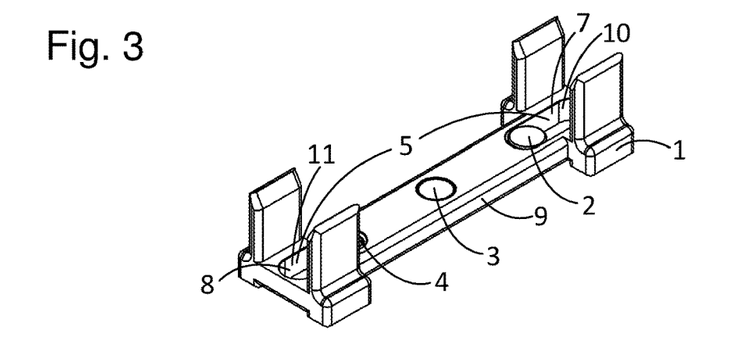
FIG. 3 illustrates a perspective view of the transport carrier of FIG. 1 without its cargo platform according to an embodiment of the present disclosure.

FIG. 3 shows the transport carrier 1 without its cargo platform 13. The transport carrier 1 can comprise a first magnetically active device 2, a second magnetically active device 3 and a third magnetically active device 4, each in form of a permanent magnet. Additionally, the transport carrier 1 can comprise a guidance 5. The guidance 5 can be adapted to guide the first magnetically active device 2 and the third magnetically active device 4. The guidance 5 can comprise a groove 10 and a groove 11 formed in the base body 9. The first magnetically active device 2 can be translationally movable arranged in the groove 10 and the third magnetically active device 4 can be translationally movable arranged in the groove 11. In one embodiment, each of the first and third magnetically active devices 2, 4 can be translationally movable along a respective straight line within the transport carrier 1. Hence, one can say, that the guidance 5 can comprise a linear guidance 7 for the first magnetically active device 2 and a linear guidance 8 for the third magnetically active device 4. These straight lines can be substantially parallel to a straight line through centers of the first magnetically active device 2, the second magnetically active device 3 and the third magnetically active device 4. The second magnetically active device 3 can be stationary fixed within the transport carrier 1, i.e. the base body 9. The third magnetically active device 4 can be mirror symmetrically arranged within the transport carrier 1 to the first magnetically active device 2 with respect to a plane through the center of the second magnetically active device 3. Hence, the transport carrier 1 can be mirror symmetrically built-up.

FIGS. 4A, 4B, 5A and 5B show the transport carrier 1 placed on a transport plane 110 of the laboratory cargo distribution system 100. The transport plane 110 can support or carry the transport carrier 1. The transport container 1 can comprise a sliding surface 15. The sliding surface 15 can be adapted to be in contact with the transport plane 110. The sliding surface 15 can enable performing translational movements of the transport carrier 1 in two dimensions on the transport plane 110 and rotational movements of the transport carrier 1 around a normal to the transport plane 110. In this embodiment, the sliding surface 15 can be an underside of the base body 9.

The laboratory cargo distribution system 100 can comprise a plurality of electro-magnetic actuators 120, 120', 120", 120''' stationary arranged below the transport plane 110, in embodiment, in a plane parallel to the transport plane 110, as apparent in FIG. 6 as well and indicated in FIGS. 4a and 5a by dashed circles. The electro-magnetic actuators 120, 120', 120", 120''' can be implemented as solenoids having a solid ferromagnetic core 125. The plurality of electro-magnetic actuators 120, 120', 120", 120''' can be arranged in rows and columns. The electro-magnetic actuators 120, 120', 120", 120''' can be equidistantly spaced within the rows and the columns by an adjacent distance AD. In each second row in each second position, there can be no electro-magnetic actuator. Thereby, the electro-magnetic actuators 120, 120', 120", 120''' can form quadrats. In each center of a quadrant, no electro-magnetic actuator can be arranged.

The electro-magnetic actuators 120, 120', 120", 120''' can be adapted to generate magnetic fields to translationally and rotationally move the transport carrier 1 on top of the transport plane 110. The first magnetically active device 2 can be adapted to interact with a first magnetic field generated by a first group of electro-magnetic actuators 120' chosen from the plurality of electro-magnetic actuators 120, 120', 120", 120''' such that a first magnetic move force can be applied to the transport carrier 1. The second magnetically active device 3 can be adapted to interact with a second magnetic field generated by a second group of electro-magnetic actuators 120" chosen from the plurality of electro-magnetic actuators 120, 120', 120", 120''' such that a second magnetic move force can be applied to the transport carrier 1. The third magnetically active 4 can be adapted to interact with a third magnetic field generated by a third group of electro-magnetic actuators 120''' chosen from the plurality of electro-magnetic actuators 120, 120', 120", 120''' such that a third magnetic move force can be applied to the transport carrier 1. The first group 120', the second group 120" and the third group 120''' of electro-magnetic actuators can be energized or driven in order to generate the first magnetic field, the second magnetic field and the third magnetic field, respectively.

Figure 4A:
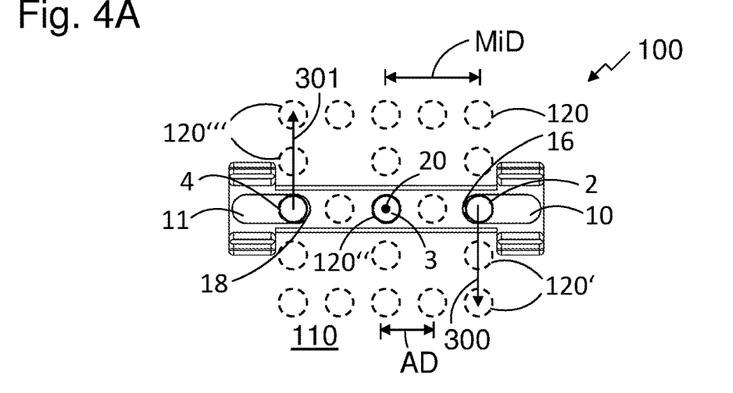
FIG. 4A illustrates a top view of the transport carrier of FIG. 3 being placed on a transport plane of a laboratory cargo distribution system according to an embodiment of the present disclosure.
Figure 4B:
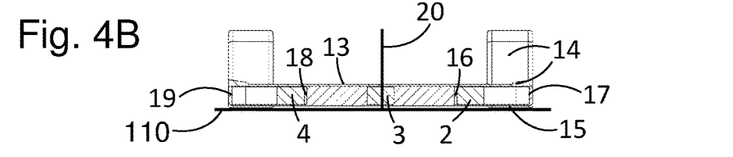
FIG. 4B illustrates a longitudinal section view of the transport carrier of FIG. 4A according to an embodiment of the present disclosure.
Figure 5A:
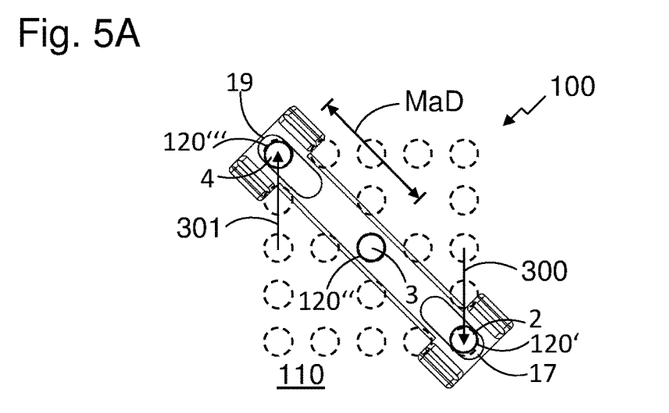
FIG. 5A illustrates a top view corresponding to FIG. 4A with the transport carrier rotated by 45° according to an embodiment of the present disclosure.
Figure 5B:
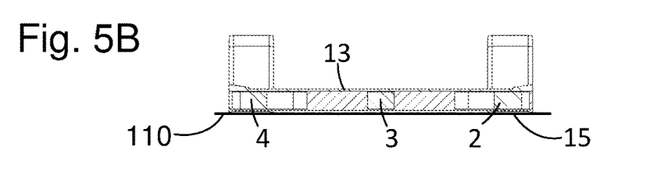
FIG. 5B illustrates a longitudinal section view of the transport carrier of FIG. 5A according to an embodiment of the present disclosure.

In FIG. 4A, each of the first, second, and third magnetically active devices 2, 3, 4 can be placed above an electro-magnetic actuator 120, 120". Beginning with this configuration, a 45° clockwise rotational movement of the transport carrier 1 around a rotational axis 20 through the center of the second magnetically active device 3 ending with the configuration shown in FIG. 5A may be performed in the following way. The first magnetically active device 2 can be successively attracted by the first group of electro-magnetic actuators 120' and hence moved downwards in FIGS. 4A, 5A as denoted by the arrow 300. Thereby, the part of the transport carrier 1 comprising the groove 10 can be moved downwards. The third magnetically active device 4 can be successively attracted by the third group of electro-magnetic actuators 120''' and hence can be moved upwards in FIGS. 4A, 5A as denoted by the arrow 301. Thereby, the part of the transport carrier 1 comprising the groove 11 can be moved upwards. The second magnetically active device 3 can be attracted by the second group of electro-magnetic actuators 120", i.e. the electro-magnetic actuator below it, and hence stationary fixed in FIGS. 4A, 5A. Thereby, the part of the transport carrier 1, in which the second magnetically active device 3 is stationary fixed, can be stationary fixed relative to the transport plane 110 and the rotational axis 20 can be defined, around which the transport carrier 1 can be rotationally moved on the transport plane 110.

The guidance 5 can enable, that a distance between the first magnetically active device 2 and the second magnetically active device 3, a distance between the first magnetically active device 2 and the third magnetically active device 4 and a distance between the third magnetically active device 4 and the second magnetically active device 3, respectively, can be variable during the rotational movement of the transport carrier 1 on the transport plane 110, as apparent in FIGS. 4A, 4B, 5A and 5B. This can enable performing the rotational movement of the transport carrier 1 on the transport plane 110 in an improved manner compared to a transport carrier comprising magnetically active devices, which can be stationary fixed within the transport carrier. A choice of electro-magnetic actuators for the first group of electro-magnetic actuators 120', the second group of electro-magnetic actuators 120" and the third group of electro-magnetic actuators 120''' for the rotational movement and a control of the rotational movement by driving the first, second and third groups 120', 120", 120''' of electro-magnetic actuators can be simplified; e.g. just the ones forming a part of a square and the one in the center of the square. The guidance 5 can enable that each of the first and third magnetically active devices 2, 4 can follow and hence can describe the part of the form of the square on the transport plane 110 during the rotation of the transport carrier 1. In detail, the linear guidances 7, 8 and, accordingly, the grooves 10, 11 can be oriented within the transport carrier 1 in such a manner, that the first and third magnetically active devices 2, 4 can translationally move parallel to the transport plane 110 within the transport carrier 1.

The guidance 5 can have a first limiting stopper 16 defining a minimum distance MiD between the first magnetically active device 2 and the second magnetically device 3 and the guidance 5 can have a second limiting stopper 17 defining a maximum distance MaD between the first magnetically active device 2 and the second magnetically device 3. Furthermore, the guidance 5 can have a third limiting stopper 18 defining a minimum distance MiD between the third magnetically active device 4 and the second magnetically device 3 and the guidance 5 can have a fourth limiting stopper 19 defining a maximum distance MaD between the third magnetically active device 4 and the second magnetically device 3. This can make it simpler to control movements of the transport carrier 1 on the transport plane 110, in particular, when the transport carrier 1 and/or the first magnetically active device 2 and/or the third magnetically active device 4 within the transport carrier 1 have been accidentally displaced. The minimum distance MiD and the maximum distance MaD can be adapted to the adjacent distance AD between the electro-magnetic actuators 120, 120', 120", 120'''. The minimum distance MiD can correspond to 2 times the adjacent distance AD plus fabrication tolerances and the maximum distance MaD corresponds to sqrt2 times the minimum distance MiD plus fabrication tolerances. This configuration can still allow each of the first and third magnetically active devices 2, 4 to describe the part of the form of the square on the transport plane 110 during the rotation of the transport carrier 1, while this configuration can also allow a better movement contribution of the magnetically active devices 2, 3, 4 to translational movements of the transport carrier 1. For example, beginning with the configuration of FIG. 4A for a translational movement of the transport carrier 1 to the left in FIG. 4A the first and second magnetically active devices 2, 3 can push the transport carrier 1.

Figure 6:
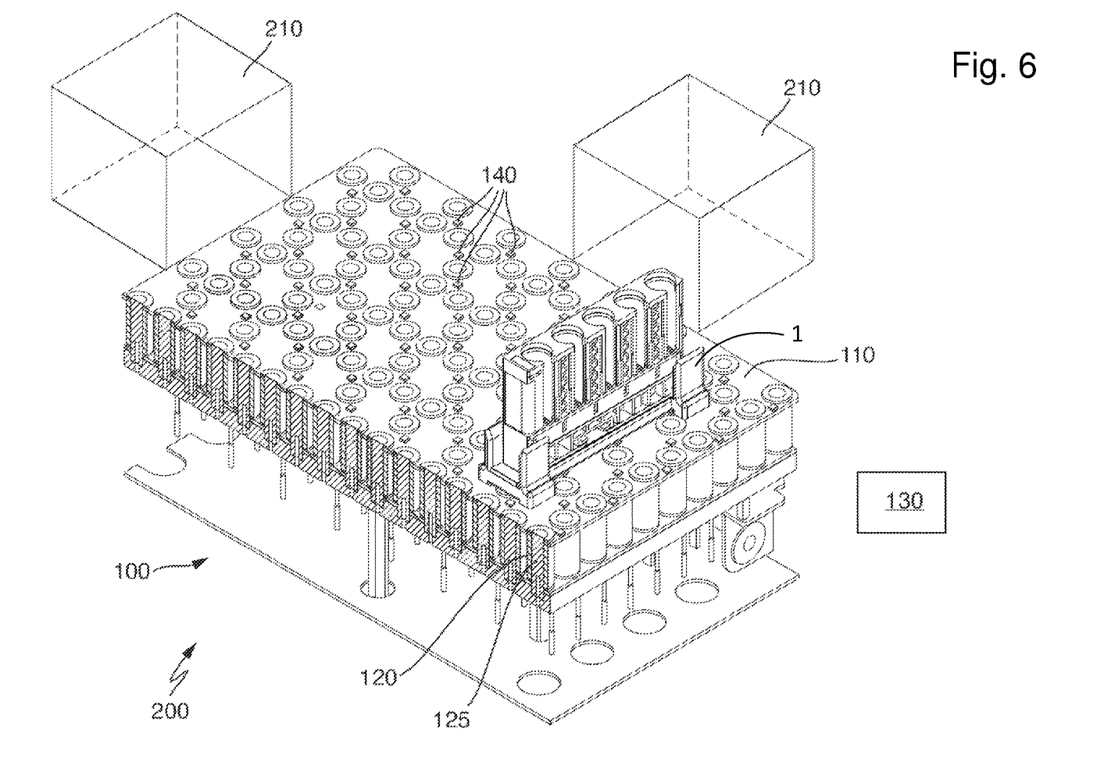
FIG. 6 illustrates a perspective view of a laboratory automation system comprising the laboratory cargo distribution system according to an embodiment of the present disclosure.

FIG. 6 shows a laboratory automation system 200 comprising the laboratory cargo distribution system 100 and a plurality of laboratory stations 210 such as, for example, in the form of pre-analytical stations, analytical stations and/or post-analytical stations. Self-evidently, more than the two laboratory stations 210 depicted in FIG. 6 may be comprised in the laboratory automation system 200. The laboratory cargo distribution system 100 can be adapted to distribute the laboratory cargo 50 by the transport carrier 1 between the laboratory stations 210. Self-evidently, more than the one transport carrier 1 depicted in FIGS. 4a to 6 may be comprised in the laboratory cargo distribution system 100. The laboratory stations 210 can be positioned adjacent to the transport plane 110 such that the transport carrier 1 can be used to transport the laboratory cargo 50 to a respective laboratory station 210.

The laboratory cargo distribution system 100 can further comprise a control device 130. The control device 130 can be configured to control translational and rotational movements of the transport carrier 1 on the transport plane 110 by driving the first group of electro-magnetic actuators 120', the second group of electro-magnetic actuators 120'' and/or the third group of electro-magnetic actuators 120''' such that the transport carrier 1 can independently move along a corresponding, in particular individual, transport path. Moreover, the laboratory cargo distribution system 100 can comprise a plurality of Hall-sensors 140. The Hall-sensors 140 can be arranged such that a position and orientation of the transport carrier 1 on the transport surface 110 can be detected.

In one embodiment, the transport carrier can comprise a first magnetically active device, a second magnetically active device and a third magnetically active device. Alternatively, the transport carrier may only comprise the first magnetically active device and the second magnetically active device or the transport carrier may comprise more than three magnetically active devices.

In one embodiment, the laboratory cargo can comprise a sample container carrier rack. Additionally or alternatively, the laboratory cargo may comprise or be a plurality of sample containers and/or laboratory equipment. The transport carrier may be adapted to carry the corresponding laboratory cargo.

As the shown and above discussed embodiments reveal, a transport carrier can be easily rotationally moved in an easily controllable manner on a transport plane of a laboratory cargo distribution system. Furthermore, a laboratory cargo distribution system can comprise such a transport carrier and a laboratory automation system can comprise such a laboratory cargo distribution system.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory cargo distribution system, the laboratory cargo distribution system comprising:
    a transport plane;
    a plurality of electro-magnetic actuators stationary arranged relative to the transport plane; and
    a transport carrier, the transport carrier comprises:
    a first magnetically active device to interact with a first magnetic field generated by a first group of electro-magnetic actuators chosen from the plurality of electro-magnetic actuators such that a first magnetic move force is applied to the transport carrier;
    a second magnetically active device to interact with a second magnetic field generated by a second group of electro-magnetic actuators chosen from the plurality of electro-magnetic actuators such that a second magnetic move force is applied to the transport carrier; and
    a guidance comprising a groove, wherein the groove elongates parallel to a longitudinal extension of the transport carrier, wherein the first magnetically active device is arranged in the groove, wherein the guidance is adapted to guide the first magnetically active device during a rotational movement of the transport carrier on the transport plane such that a distance between the first magnetically active device and the second magnetically active device is variable parallel to the transport plane when the transport carrier is placed on the transport plane, wherein the transport carrier carries a laboratory cargo and moves over the transport plane.

2. The laboratory cargo distribution system according to claim 1, wherein the guidance comprises a linear guidance such that the first magnetically active device is translationally movable along a straight line within the transport carrier, wherein the straight line is parallel to a straight line between the first magnetically active device and the second magnetically active device.

3. The laboratory cargo distribution system according to claim 1, wherein the transport carrier further comprising a base body.

4. The laboratory cargo distribution system according to claim 3, wherein the groove is formed in the base body.

5. The laboratory cargo distribution system according to claim 1, wherein the transport carrier further comprising,
    a cargo platform, wherein the cargo platform carries the laboratory cargo; and
    a plurality of fixing devices to fix the laboratory cargo relative to the cargo platform.

6. The laboratory cargo distribution system according to claim 1, wherein the transport carrier further comprising,
    a sliding surface, wherein the sliding surface is adapted to be in contact with the transport plane when the transport carrier is placed on the transport plane.

7. The laboratory cargo distribution system according to claim 1, wherein the second magnetically active device is stationary fixed within the transport carrier.

8. The laboratory cargo distribution system according to claim 1, wherein the guidance has a first limiting stopper defining a minimum distance (MiD) between the first magnetically active device and the second magnetically device and wherein the guidance has a second limiting stopper defining a maximum distance (MaD) between the first magnetically active device and the second magnetically device.

9. The laboratory cargo distribution system according to claim 1, wherein the transport carrier further comprising,
a third magnetically active device to interact with a third magnetic field generated by a third group of electro-magnetic actuators chosen from the plurality of electro-magnetic actuators such that a third magnetic move force is applied to the transport carrier, wherein the guidance is adapted to guide the third magnetically active device such that a distance between the first magnetically active device and the third magnetically active device and/or a distance between the second magnetically active device and the third magnetically active device is variable during a rotational movement of the transport carrier on the transport plane.

10. The laboratory cargo distribution system according to claim 1, wherein the guidance comprises a slot hole, wherein a width of the slot hole fits with an elongation of the first magnetically active device, wherein the first magnetically active device is arranged in the slot hole, wherein the slot hole elongates parallel to a longitudinal extension of the transport carrier.

11. A laboratory cargo distribution system, wherein the laboratory cargo distribution system comprises:
a transport plane;
a plurality of electro-magnetic actuators stationary arranged relative to the transport plane; and
a transport carrier, wherein the transport carrier comprises,
a first magnetically active device to interact with a first magnetic field generated by a first group of electro-magnetic actuators chosen from the plurality of electro-magnetic actuators such that a first magnetic move force is applied to the transport carrier,
a second magnetically active device to interact with a second magnetic field generated by a second group of electro-magnetic actuators chosen from the plurality of electro-magnetic actuators such that a second magnetic move force is applied to the transport carrier, and
a guidance comprising a groove, wherein the groove elongates parallel to a longitudinal extension of the transport carrier, wherein the first magnetically active device is arranged in the groove, wherein the guidance is adapted to guide the first magnetically active device during a rotational movement of the transport carrier on the transport plane such that a distance between the first magnetically active device and the second magnetically active device is variable, wherein the transport carrier carries a laboratory cargo and moves over the transport plane,
wherein the guidance has a first limiting stopper defining a minimum distance (MiD) between the first magnetically active device and the second magnetically device and wherein the guidance has a second limiting stopper defining a maximum distance (MaD) between the first magnetically active device and the second magnetically device, wherein the plurality of electro-magnetic actuators is arranged in rows and columns, wherein the electro-magnetic actuators are equidistantly spaced within the rows and the columns by an adjacent distance (AD),
wherein the minimum distance (MiD) corresponds to the adjacent distance (AD) or a multiple of the adjacent distance (AD), and wherein the maximum distance (MaD) corresponds to sqrt2 times the minimum distance (MiD).

* * * * *